United States Patent
Vogt et al.

(10) Patent No.: US 9,192,565 B2
(45) Date of Patent: Nov. 24, 2015

(54) ALCOHOL-FREE MOUTHWASH

(75) Inventors: Robert Vogt, Princeton Junction, NJ (US); Karsten Kohrs, Berkeley Heights, NJ (US); Evangelia S. Arvanitidou, Princeton, NJ (US); Fernando Perna, Sau Paulo (BR)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/356,637

(22) PCT Filed: Nov. 9, 2011

(86) PCT No.: PCT/US2011/059865
§ 371 (c)(1),
(2), (4) Date: May 7, 2014

(87) PCT Pub. No.: WO2013/070198
PCT Pub. Date: May 16, 2013

(65) Prior Publication Data
US 2014/0286880 A1    Sep. 25, 2014

(51) Int. Cl.
*A61K 8/92*     (2006.01)
*A61K 8/34*     (2006.01)
*A61K 8/41*     (2006.01)
*A61Q 11/00*    (2006.01)
*A61K 8/06*     (2006.01)
*A61K 8/21*     (2006.01)
*A61K 8/49*     (2006.01)
*A61K 8/60*     (2006.01)

(52) U.S. Cl.
CPC ............ *A61K 8/922* (2013.01); *A61K 8/064* (2013.01); *A61K 8/068* (2013.01); *A61K 8/21* (2013.01); *A61K 8/34* (2013.01); *A61K 8/345* (2013.01); *A61K 8/416* (2013.01); *A61K 8/4926* (2013.01); *A61K 8/60* (2013.01); *A61Q 11/00* (2013.01); *A61K 2800/30* (2013.01); *A61K 2800/5922* (2013.01)

(58) Field of Classification Search
USPC ....................................... 424/52
See application file for complete search history.

(56) References Cited

U.S. PATENT DOCUMENTS

| | | | |
|---|---|---|---|
| 5,283,056 A | 2/1994 | Chung et al. | |
| 5,560,906 A | 10/1996 | Scodari et al. | |
| 5,624,906 A * | 4/1997 | Vermeer | 514/23 |
| 6,207,192 B1 | 3/2001 | Lau | |
| 2005/0169852 A1 | 8/2005 | Roberge et al. | |
| 2007/0166242 A1* | 7/2007 | Kross | 424/48 |

FOREIGN PATENT DOCUMENTS

| | | |
|---|---|---|
| CN | 1137705 | 11/1996 |
| JP | 4-202121 | 7/1992 |
| JP | 2011-148770 | 8/2011 |
| JP | 2012-136504 | 7/2012 |
| WO | WO 94/01081 | 1/1994 |
| WO | WO 95/17159 | 6/1995 |
| WO | WO 9517159 A1 * | 6/1995 |
| WO | WO 99/43290 | 9/1999 |
| WO | WO 2004/045572 | 6/2004 |
| WO | 2004/073669 | 9/2004 |
| WO | WO 2012/132747 | 10/2012 |

OTHER PUBLICATIONS

International Search Report and the Written Opinion issued in International Application PCT/US11/59865 mailed Sep. 5, 2012. WO.
Written Opinion of the International Preliminary Examining Authority issued in International Application PCT/US11/59865 mailed Oct. 18, 2013.

* cited by examiner

*Primary Examiner* — Frederick Krass
*Assistant Examiner* — Amanda Heyes

(57) ABSTRACT

The invention provides ethanol-free liquid oral care compositions comprising cetyl pyridinium chloride which do not have an unacceptably bitter taste, e.g. mouthwashes, toothpastes, throat sprays, and breath sprays that are substantially free of ethanol, e.g., comprising (i) an antimicrobially effective amount of cetyl pyridinium chloride (CPC), (ii) one or more flavoring oils which are substantially insoluble in water at room temperature, and (iii) water, wherein the ratio of the CPC to the one or more flavoring oils is from 1:1.5 to 1:2.5, as well as methods of making and using the same.

18 Claims, No Drawings

ALCOHOL-FREE MOUTHWASH

FIELD OF THE INVENTION

The present invention relates to novel liquid alcohol-free oral care compositions comprising cetylpyridinium chloride.

BACKGROUND OF THE INVENTION

Conventional mouthwash compositions frequently contain ethanol, up to 27% volume, as a preservative and antimicrobial agent. In some individuals, alcohol may exacerbate xerostomia (dry mouth), which in turn can cause halitosis and significant tooth decay, as the protective effect of saliva's remineralizing the enamel is reduced. Xerostomia also makes the mucosa and periodontal tissue of the mouth more vulnerable to infection and increases the risk of gingivitis. Mouthwash comprising high levels of alcohol also may be undesirable for use by alcoholics, children, and members of certain religious faiths, and some consumers may object to the burning sensation of relatively high alcohol compositions.

Cetylpyridinium chloride (CPC) is a cationic quaternary ammonium compound frequently used in addition to or in place of ethanol as an antiseptic and preservative in mouthwashes, toothpastes, lozenges, throat sprays, breath sprays, and nasal sprays. At effective concentrations, e.g. ca. 0.07%, CPC kills bacteria and other microorganisms and has been shown to be effective in preventing dental plaque and reducing gingivitis. It is believed to kill bacteria by binding to the negatively charged phosphates of the bacterial cell membrane. Formulating CPC presents challenges, however, because of its bitter taste and its incompatibility with many composition excipients. Ethanol can be helpful in such compositions as it acts as a solubilizer for many ingredients and is a flavor enhancer, but a noted above, there are disadvantages to oral care products comprising ethanol.

There is a need for ethanol-free liquid oral care compositions having an acceptable taste.

BRIEF SUMMARY OF THE INVENTION

The invention provides ethanol-free liquid oral care compositions comprising CPC that do not have an unacceptably bitter taste. This is accomplished by admixing relatively insoluble flavoring oils with the CPC in a particular ratio. For example, the invention provides a liquid oral care composition which is substantially free of ethanol, comprising (i) an antimicrobially effective amount of cetyl pyridinium chloride (CPC) and (ii) one or more flavoring oils which are substantially insoluble in water at room temperature, wherein the ratio of the CPC to the one or more flavoring oils is from 1:1.5 to 1:2.5. Without intending to be bound by theory, it is believed, that at optimal concentrations, the CPC and the one or more flavoring oils spontaneously or with gentle mixing can form a stable micelle or a water-in-oil microemulsion at room temperature in the presence of water, which helps mask the bitter taste of the CPC without affecting its efficacy as an antibacterial agent, and at the same time, the surfactant properties of the CPC allow elevated levels of poorly soluble oils which themselves may have antibacterial properties.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION OF THE INVENTION

In one embodiment, the invention provides a liquid oral care composition (Composition 1) which is substantially free of ethanol, e.g., less than 5% ethanol, comprising (i) an antimicrobially effective amount of cetyl pyridinium chloride (CPC), and (ii) one or more flavoring oils which are substantially insoluble, E.g., less than 1% soluble, in water at room temperature, wherein the ratio of the CPC to the one or more flavoring oils is from 1:1.5 to 1:2.5. For example, the invention provides 1.1. The liquid, oral care composition of Composition 1 wherein the ratio of the CPC to the one or more flavoring oils is 1:1.6 to 1:1.9.
1.2. The liquid oral care composition of Composition 1 or 1.1 wherein the CPC and the one or more flavoring oils form a micelle or a water-in-oil microemulsion in aqueous media at room temperature.
1.3. The liquid oral care composition of any of the foregoing Compositions wherein the one or more flavoring oils comprise menthol.
1.4. The liquid, oral care composition of any of the foregoing Compositions wherein the one or more flavoring oils comprise menthol, spearmint oil, peppermint oil, or combinations of any of these.
1.5. The liquid oral care composition of any of the foregoing Compositions wherein the one of more flavoring oils are selected from one or more of menthol, spearmint oil, peppermint oil, carvone, methyl salicylate, anethole, thymol, eugenol, coolants, cinnamic aldehydes, and mixtures thereof.
1.6. The liquid oral care composition of any of the foregoing Compositions wherein the one or more flavoring oils comprise a combination of menthol, spearmint oil and peppermint oil in a ratio to CPC as follows:
   1 part CPU:
   0.3-0.9 parts menthol:
   0.4-1.2 parts spearmint oil:
   0.1-0.5 parts peppermint oil.
1.7. The liquid oral care composition of any of the foregoing Compositions that is substantially free of ethanol and that comprises
   an antimicrobially effective amount of cetylpyridinium chloride (e.g., 0.05-0.1%/weight, e.g., 0.07-0.08%, about 0.075% by weight), and
   an effective amount of a flavoring component (e.g., 0.05-0.3%, e.g., 0.1-0.2%, e.g. about 0.12% by weight of total composition), the flavoring component comprising
      menthol, e.g. in an amount of at least 15%, 15-25%, e.g. about 20% by weight of flavoring component;
      peppermint oil (e.g., natural peppermint oil, synthetic peppermint oil, cornmint oil or mixtures thereof), e.g., in an amount of at least 10%, e.g., 10-20%, e.g., about 15% by weight of flavoring component;
      spearmint oil, e.g., in an amount of 0-55%, e.g., 40-50%, about 45% by weight of flavoring component;
1.8. The liquid oral care composition of any of the foregoing Compositions (e.g. mouthwashes, toothpastes, throat sprays, and breath sprays) being substantially free of ethanol and comprising an antimicrobially effective amount of a CPC and flavorants in the following ratio:
   1 part CPC:
   0.3-0.9, e.g., 0.5-0.7 parts menthol:
   0.4-1.2, e.g., 0.5-0.8 parts spearmint oil:
   0.1-0.5, e.g., 0.2-0.4 parts peppermint oil;

and optionally further ingredients, e.g. further comprising one or more of additional flavorants, e.g., comprising one or more of anethole (e.g., trans-anethole), thymol, methyl salicylate, coolants (for example n-ethyl-p-menthane-3-carboxamide, Optacool®), cinnamic aldehydes and mixtures thereof;

additional preservatives, e.g, paraben preservatives, for example methyl p-hydroxybenzoate, propyl p-hydroxybenzoate, and mixtures thereof;

non-caloric sweeteners, e.g., comprising saccharin, sugar alcohols (e.g., sorbitol), or mixtures thereof;

humectants, e.g., comprising propylene glycol, glycerin or mixtures thereof;

non-ionic surfactants, e.g., poloxamers, e.g., poloxamer 470;

a fluoride ion source, e.g, sodium fluoride; and water.

1.9. The liquid oral care composition of any of the foregoing Compositions in the form of a mouthwash;

1.10. The liquid oral care composition of any of the foregoing Compositions comprising CPC and a flavor component comprising flavorants in a ratio of CPC and flavorants by weight is about 1 part CPC about 0.3 parts menthol:about 0.7 parts spearmint oil:about 0.24 parts peppermint oil; wherein the composition may optionally comprise coolants and/or sweeteners in addition to the flavor component.

1.11 The liquid oral care composition of any of the foregoing Compositions wherein the flavor component comprises by weight of flavor component about 20% menthol, about 45% spearmint oil and about 15% peppermint oil;

1.12. The liquid oral care composition of any of the foregoing Compositions comprising L-menthol, 1.13. The liquid oral care composition of any of the foregoing Compositions comprising menthol in addition to the menthol in the flavoring component, e.g., 0.01-0.04, e.g., about 0.02% menthol by weight of the total composition, in addition to the menthol in the flavoring component;

1.14. A composition according to any of the preceding compositions comprising 0.05-0.07% total menthol, e.g., including added menthol and menthol from peppermint oil and spearmint oil 1.15. A composition according to any of the preceding embodiments wherein the flavoring component further comprises an anethole, e.g., trans-anethole, in an amount of 1-10%, e.g., 2-6%, e.g., about 4% by weight of flavoring component; or 0.001-0.01%, e.g., 0.002-0.006% e.g., about 0.004% by weight of the total composition;

1.16. A composition according to any of the preceding embodiments which is an aqueous solution, water-in-oil emulsion, water-in-oil microemulsion, or micellar system;

1.17. A composition according to any of the preceding embodiments which is a water-in-oil microemulsion;

1.18. A composition according to any of the preceding embodiments which is a micellar system;

1.19. A composition according to any of the preceding embodiments further comprising additional flavorants, e.g., comprising one or more of anethole (e.g., trans-anethole), thymol, coolants (for example comprising menthol, n-ethyl-p-menthane-3-carboxamide, and combinations thereof), cinnamic aldehydes and mixtures thereof, for example coolant mixtures available commercially, e.g. Optacool® (Symrise);

1.20. A composition according to any of the preceding embodiments further comprising additional preservatives, e.g., paraben preservatives, for example methyl p-hydroxybenzoate, propyl p-hydroxybenzoate, and mixtures thereof;

1.21. A composition according to any of the preceding embodiments further comprising non-caloric sweeteners, e.g., comprising saccharin, sugar alcohols (e.g., sorbitol), or mixtures thereof.

1.22. A composition according to any of the preceding embodiments further comprising humectants, e.g., comprising propylene glycol, glycerin or mixtures thereof;

1.23. A composition according to any of the preceding embodiments comprising water, colorant, sodium saccharide, sodium fluoride, CPC, poloxamer, e.g., Pluronic. F-127, sorbitol, glycerin, propylene glycol, parabens, and menthol, wherein the composition is substantially clear.

1.24 A composition according to any of the preceding embodiments further comprising non-ionic surfactants, e.g., poloxamers, e.g., poloxamer 470;

1.25. A composition according to any of the preceding embodiments further comprising a fluoride ion source, e.g., sodium fluoride;

1.26, A composition according to any of the preceding embodiments which is an aqueous solution, water-in-oil emulsion, or water-in-oil microemulsion;

1.27. A composition according to any of the foregoing embodiments comprising the following ingredients, by weight:

| | |
|---|---|
| i) sorbitol | 4-7%, |
| ii) humectant, e.g. glycerin, propylene glycol and combinations thereof | 12-18% |
| iii) sodium fluoride | 0.04-0.06% |
| iv) cetylpyridinium chloride | 0.05-0.1% |
| v) sodium saccharin | 0.01-0.03% |
| vi) polaxamer 407 | 0.3-0.5% |
| vii) flavoring component | 0.05-0.5%, e.g., 0.1-0.3% |
| viii) menthol/coolant (in addition to flavoring component) | 0.02-0.06% |
| ix) dye | 0.0-0.01% |
| x) parabens | 0.02-0.06% |
| xi) water | 75-85% | wherein the flavor component comprises 85-100% insoluble flavoring oils.

1.28. A composition according to any of the preceding embodiments comprising the following ingredients, by weight:

| | |
|---|---|
| sorbitol | 3-5% . e.g., about 4% |
| glycerin | 6-9%, e.g., about 7.5% |
| propylene glycol | 6-8%, e.g., about 7% |
| sodium fluoride | 0.04-0.06%, e.g., about 0.05% |
| cetylpridinium chloride | 0.05-0.1%, e.g., about 0.075% |
| sodium saccharin | 0.01-0.03%, e.g., about 0.2% |
| polaxamer 407 | 0.3-0.5%, e.g., about 0.4% |
| flavoring component | 0.05-0.5, e.g., 0.1-0.3%, e.g., about 0.12% |
| menthol/coolant (in addition to flavoring component) | 0.02-0.06%, e.g., about 0.045% |
| dye | 0.0-0.01, e.g., about 0.001% |
| parabens, e.g., (about 3:1 methyl p-hydroxybenzoate:propyl-p-hydroxybenzoate) | 0.02-0.06%, e.g., about 0.04% |
| water | 75-85%, e.g., balance | wherein the flavor component comprises:

| | |
|---|---|
| L-menthol | 15-25%, e.g. about 20% |
| N-ethyl-p-menthane-3-carboxamide | 1-3%, e.g., about 2% |
| trans-anethole | 2-6%, e.g., about 4% |
| eugenol | 0.1-0.3%, e.g., about 0.2% |
| Peppermint oil (e.g., 2:1. cornmint oil:synthetic peppermint oil) | 10-20%, e.g., about 15% |
| thymol | 0.2-0.6%, e.g., about 0.4% |
| methyl salicylate | 10-15%, e.a.. about 1.3% |
| cinnamic aldehydes | 0.1-0.3%, e.g., about 0.2% |
| spearmint oil | 35-55%, e.g., about 45% |

The invention further provides methods of prophylaxis and/or treatment of a disease or condition selected from one or more of dry mouth, halitosis, gingivitis, tooth decay, and cavities, comprising administering an effective amount of a composition as hereinbefore described, e.g. any of Compositions 1, 1.1, et seq., to a subject in need thereof.

The invention further provides the use of cetyl pyridinium chloride (CPC) and one or more flavoring oils which are substantially insoluble in water at room temperature, in a ratio of the CPC to the one or more flavoring oils from 1:1.5 to 1:2.5, in the manufacture of a liquid oral care composition, e.g. any of Compositions 1, 1.1 et seq., for prophylaxis and/or treatment of a disease or condition selected from one or more of dry mouth, halitosis, gingivitis, tooth decay, and cavities.

The invention further provides a method of making a composition e.g. any of Compositions 1, 1.1, et seq., comprising adding flavoring oils, to an aqueous solution comprising cetylpyridinium chloride and mixing until the composition is clear, e.g., a method comprising adding colorant to water and mixing, then adding sodium saccharide, sodium fluoride and CPC and mixing, then adding a poloxamer, e.g., Pluronic F-127 and mixing, then adding add sorbitol and glycerin and mixing, and then adding a mixture of propylene glycol, parabens, and menthol and other flavorings, and mixing until the composition is clear.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLE 1

Comparative Compositions

Compositions are prepared with different flavoring oils as follows:

TABLE 1

Mouthrinse compositions

| Ingredient | Formula A (%) | Formula B (%) |
|---|---|---|
| Sorbitol (70% solution) | 5.5 | 5.5 |
| Glycerin | 7.5 | 7.5' |
| Propylene glycol | 7.0 | 7.0 |
| Sodium fluoride | 0.05 | 0.5 |

TABLE 1-continued

Mouthrinse compositions

| Ingredient | Formula A (%) | Formula B (%) |
|---|---|---|
| Cetylpyridinium chloride | 0.075 | 0.075 |
| Sodium saccharin | 0.022 | 0.022 |
| Poloxamer 407' | 0.4 | 0.4 |
| Flavor A | 0.12 | — |
| Flavor B | — | 0.12 |
| Menthol | 0.02 | 0.02 |
| Coolant blend (Optacool ®) | 0.025 | 0.025 |
| Dye | 0.01 | 0.001 |
| Methyl-p-hydroxybenzoate | 0.03 | 0.03 |
| Propyl-p-hydroxybenzoate | 0.01 | 0.01 |
| Water | balance | balance |

TABLE 2

Flavoring components

| Ingredient | Formula A (%) | Formula B (%) |
|---|---|---|
| L-menthol | 20 | 15 |
| North American peppermint oil | — | 9 |
| North American spearmint oil | 45 | 56 |
| Synthetic peppermint oil | 5 | — |
| Cornmint oil | 10 | — |
| N-ethyl-p-menthane-3-carboxamide | 2 | 2 |
| Trans-anethole | 4 | 4 |
| Eugenol | 0.2 | 0.2 |
| Thymol | 0.4 | 0.4 |
| Cinnamic aldehydes | 0.2 | 0.2 |
| Methyl salicylate | 13.2 | 13.2 |

EXAMPLE 2

Consumer Testing

The compositions of the previous example were tested with consumers to measure flavor liking and purchase intent.

TABLE 3

Consumer test results

| Ingredient | Formula A | Formula B |
|---|---|---|
| Purchase Intent (Definitely would buy - Top Box) | 85% | 76% |
| Has taste I like | 87% | 80% |
| Gives long-lasting freshness | 85% | 74% |
| Intensity of flavor - Like it a lot | 87% | 74% |

Generally, the more acceptable composition, Formula A, had higher levels of menthol and peppermint oil relative to spearmint oil. Spearmint oil and peppermint oil differ, inter alia, in that peppermint oil has higher amounts of menthol. This difference, coupled with the higher level of added menthol, means that Formula A had significantly more menthol than Formula B.

Without being bound by theory, it is hypothesized that the relatively higher levels of poorly soluble menthol in Formula A permit formation of a spontaneous microemulsion or micellar system incorporating the CPC, reducing the perception of bitter taste from the CPC. At the same time, the CPC allows the composition to contain higher levels of poorly soluble oils such as menthol, which themselves have antibacterial properties, thereby enhancing the efficacy of the composition.

EXAMPLE 3

Flavor Refinement

Further flavorings were tested in the above mouthwash composition, confirming that CPC compositions comprising higher levels of insoluble or poorly soluble oils are preferred by consumers. Mouthwashes with the following flavoring compositions were consumer tested (ingredients given as percent by weight of flavoring):

TABLE 3

Flavoring components

| Ingredient | Flavor C | Flavor D | Flavor E | Flavor F |
|---|---|---|---|---|
| L-menthol | 20 | 43 | 18 | 14 |
| N-ethyl-p-menthane-3-carboxamide | 7 | 1 | 2 | 1.6 |
| 2-isopropyl-N,2,3-trimethylbutyramide | 7 | | | |
| Trans-anethole | 5 | 6 | 2 | 1.6 |
| Eugenol | 1 | 1 | | |
| Optacool Special C flavor | 10 | 7 | | |
| Optamint flavor | 20 | 12 | | |
| BrightStar 7.0 | 20 | | | |
| Cornmint oil | 10 | 13 | | |
| Methyl salicylate | | | 14 | 14.2 |
| Peppermint flavor | | | 3 | 2.4 |
| L-carvone | | | 33 | 30 |
| Soft mint combo | | | 16 | 13.8 |
| Artificial alcohol replacer | | | | 12 |
| Total percent poorly soluble oils other than added menthol | 66 | 37 | 80 | 71.6 |
| Total percent poorly soluble oils including added menthol | 86 | 80 | 98 | 85.6 |

Mouthrinse with flavoring C is compared to mouthrinse with flavoring D, and mouthrinse with flavoring E is compared to mouthrinse with flavoring F. Consumers show a marked preference for C over D and for E over F, confirming that the products having higher levels of insoluble or poorly soluble oils are preferred, and that there is a preferred range for menthol in the flavoring, e.g., greater than 15% but less than 43%, preferably about 18-20%, in addition to the menthol present in the mint oil and in the base formulation. In the base formulations used, which comprise 0.12% flavor and 0.02% added menthol, this corresponds to a total of 0.042-0.044% menthol in the formulation, plus the menthol present in the mint oils. The overall ratio of CPC (0.075%) to insoluble oils (0.12-0.14%) in the formulation would thus be from 1:1.6 to 1:1.9.

The invention claimed is:

1. A liquid oral care composition having less than 5% wt. of ethanol, comprising
   (i) an antimicrobially effective amount of cetyl pyridinium chloride (CPC), and
   (ii) one or more flavoring oils which are substantially insoluble in water at room temperature, wherein the ratio of the CPC to the one or more flavoring oils is from 1:1.5 to 1:2.5, and wherein the one or more flavoring oils comprise menthol, peppermint oil and spearmint oil, wherein the CPC and the one or more flavoring oils form a micelle or a water-in-oil microemulsion in aqueous media at room temperature.

2. The liquid oral care composition of claim 1 wherein the ratio of the CPC to the one or more flavoring oils is 1:1.6 to 1:1.9.

3. The liquid oral care composition of claim 1 wherein the composition comprises coolants and/or sweeteners in addition to menthol, peppermint oil and spearmint oil.

4. The liquid oral care composition of claim 1 wherein the one or more flavoring oils comprise a combination of menthol, spearmint oil and peppermint oil in a ratio to CPC as follows:
   1 part CPC:
   0.3-0.9 parts menthol:
   0.4-1.2 parts spearmint oil:
   0.1-0.5 parts peppermint oil.

5. The liquid oral care composition of claim 1 wherein the one or more flavoring oils comprise:
   i) menthol in an amount of at least 15% by weight;
   ii) peppermint oil in an amount of at least 10% by weight;
   iii) spearmint oil in an amount of 30-55% by weight.

6. The liquid oral care composition of claim 1 in the form of a mouthrinse.

7. The liquid oral care composition of claim 1 comprising 0.05-0.07% total menthol.

8. The liquid oral care composition of claim 1 further comprising one or more of carvone, methyl salicylate, anethole, thymol, eugenol, or coolants, wherein the coolants are in addition to menthol, peppermint oil, and spearmint oil, cinnamic aldehydes, and mixtures thereof.

9. The liquid oral care composition of claim 1 further comprising one or more parabens.

10. The liquid oral care composition of claim 1 further comprising non-caloric sweeteners selected from saccharin, sugar alcohols, and mixtures thereof.

11. The liquid oral care composition of claim 1 further comprising humectants, selected from propylene glycol, glycerin or mixtures thereof.

12. The liquid oral care composition of claim 1 further comprising one or more poloxamers.

13. The liquid oral care composition of claim 1 further comprising an effective concentration of a fluoride ion source.

14. The liquid oral care composition of claim 1 comprising the following ingredients, by weight:

| | | |
|---|---|---|
| i) | sorbitol | 4-7% |
| ii) | glycerin, propylene glycol and combinations thereof | 12-18% |
| iii) | sodium fluoride | 0.04-0.06% |
| iv) | cetylpyridinium chloride | 0.05-0.1% |
| v) | sodium saccharin | 0.01-0.03% |
| vi) | polaxamer 407 | 0.3-0.5% |
| vii) | flavoring component | 0.1-0.3% |
| viii) | menthol/coolant (in addition to flavoring component) | 0.02-0.06% |
| ix) | dye | 0.0-0.01% |
| x) | parabens | 0.02-0.06% |
| xi) | water | 75-85% | wherein the flavoring component (vii) comprises 85-100% insoluble flavoring oils.

15. A method of prophylaxis and/or treatment of a disease or condition selected from one or more of dry mouth, halitosis, gingivitis, tooth decay, and cavities, comprising administering an effective amount of the liquid oral care composition according to claim 1 to a subject in need thereof.

16. A method of making the liquid oral care composition according to claim 1 comprising adding flavoring oils to an aqueous solution comprising cetylpyridinium chloride and mixing until the composition is clear.

17. The method of claim 16 comprising adding colorant to water and mixing, then adding sodium saccharide, sodium fluoride and CPC and mixing, then adding a poloxamer and mixing, then adding sorbitol and glycerin and mixing, and then adding a mixture of propylene glycol, parabens, and menthol and other flavorings, and mixing until the composition is clear.

18. The liquid oral care composition of claim 2 wherein the one or more flavoring oils comprise a combination of menthol, spearmint oil and peppermint oil in a ratio to CPC as follows:

1 part CPC:
0.3-0.9 parts menthol:
0.4-1.2 parts spearmint oil:
0.1-0.5 parts peppermint oil;
wherein the flavoring component comprises
i) menthol in an amount of 15-25% by weight of the flavoring component;
ii) peppermint oil in an amount of 10-20% by weight of the flavoring component;
iii) spearmint oil in an amount of 40-50% by weight of the flavoring component.

\* \* \* \* \*